United States Patent [19]

Immler et al.

[11] 4,187,304
[45] Feb. 5, 1980

[54] PROCEDURE FOR TREATING MAMMALS TO CONTROL PARASITIC DIPTERA LARVAE

[75] Inventors: Rolf Immler, Arisdorf; Hans Bouvard, Ollon, both of Switzerland

[73] Assignee: Ciba-Geigy Corporation, Ardsley, N.Y.

[21] Appl. No.: 10,277

[22] Filed: Feb. 7, 1979

[30] Foreign Application Priority Data

Feb. 17, 1978 [CH] Switzerland .......................... 1761/78

[51] Int. Cl.² .......................................... A61K 31/53
[52] U.S. Cl. ................................................ 424/249
[58] Field of Search ..................................... 424/249

[56] References Cited

PUBLICATIONS

Brechbuhler et al., Chem. Abst., vol. 88 (1978) p.152,673b.

*Primary Examiner*—Sam Rosen
*Attorney, Agent, or Firm*—Frederick H. Rabin

[57] ABSTRACT

The present invention relates to a procedure for treating domestic animals and productive livestock belonging to the class of Mammalia (mammals) for systemic control of tissue-parasitic insect larvae of the order of Diptera, which comprises parenteral or transcutaneous administration to the animals to be treated of an effective dose of an active substance of the general formula I

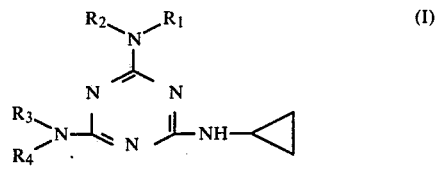

in which $R_1$ is hydrogen, methyl, ethyl or cyclopropyl, $R_2$ is hydrogen or methyl, $R_3$ is hydrogen, methyl or cyclopropyl and $R_4$ is hydrogen or methyl, or of an an acid addition salt thereof which is non-toxic to mammals or of a composition which contains the active substance or an acid addition salt thereof which is non-toxic to mammals.

4 Claims, No Drawings

PROCEDURE FOR TREATING MAMMALS TO CONTROL PARASITIC DIPTERA LARVAE

The present invention relates to a procedure for treating domestic animals and productive livestock belonging to the class of Mammalia (mammals) for systemic control of tissue-parasitic insect larvae of the order of Diptera, which comprises parenteral or transcutaneous administration to the animals to be treated of an effective dose of an active substance of the general formula I

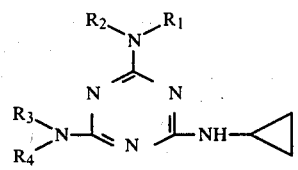 (I)

in which $R_1$ is hydrogen, methyl, ethyl or cyclopropyl, $R_2$ is hydrogen or methyl, $R_3$ is hydrogen, methyl or cyclopropyl and $R_4$ is hydrogen or methyl, or of an acid addition salt thereof which is non-toxic to mammals or of a composition which contains the active substance or an acid addition salt thereof which is non-toxic to mammals.

The term acid addition salts of compounds of the formula I is to be understood as meaning salts with pharmaceutically acceptable acids, for example with strong mineral acids, such as hydrochloric acid or sulfuric acid, or with organic acids, such as acetic acid, tartaric acid or citric acid.

Amongst the compounds of the formula I, 2,4-diamino-6-cyclopropylamino-s-triazine is very particularly suitable for control of tissue-parasitic insect larvae of the order of Diptera, because of its outstanding action.

The control of Diptera larvae, which live as parasites in the tissues of their host animals, is of extremely great importance, especially in view of the considerable damage which can be caused by the parasites in productive livestock husbandry and very particularly in the husbandry of grazing animals.

The Diptera larvae can find their way into the tissues of their host animals in very diverse ways. Thus, after oviposition by the Diptera females, which can take place at various parts of the body of the host animals, the larvae hatched from the eggs can be taken in by the host animals by licking and bore into the pharynx, or the larvae can bore into the skin of the host animals from the outside. However, the eggs can also first be deposited on mosquitoes or flies. The larvae develop in the eggs and hatch as soon as the carrier insect seeks out a suitable host animal. In the case of the viviparous Diptera species the larvae can be introduced direct by the Diptera females into the nose or the eyes of the host animals.

After the larvae have passed into the host animals, they can, by migration, seek out those parts of the body which they prefer. The larvae can be present, for example, in or under the skin, in the gastro-intestinal tract or in the nasal cavities, the cavity of the pharynx or the frontal sinus of their hosts.

The various types of parasitism by Diptera larvae in animals are termed myiases.

Myiases can occur in numerous species of animals, for example in cattle, horses, donkeys, mules, reindeer, sheep, pigs, dogs and cats.

In the host animals, the infestation by parasitic Diptera larvae can lead, in addition to other adverse effects, to a reduction in the milk yield, to loss of wool, loss of weight or even to death. If the host animals are infested by skin parasites which cause swellings to form in the skin, this can also result in depreciation in the value of the skins due to perforation, since the swellings have a small orifice which is enlarged by the larvae before they leave the host for pupation.

Since the larvae can infest very diverse parts of the body of the host animals, some of which parts are not readily accessible, their control is highly problematical.

It has now been found that, surprisingly, compounds of the formula I, including their acid addition salts which are non-toxic to mammals and compositions which contain these compounds as active ingredients, are outstandingly suitable for the control of parasitic Diptera larvae. The substances develop a systemic action which means that even on local application to the host animal an action against the parasitic Diptera larvae takes place even in parts of the body which have not been treated. The procedure according to the invention thus enables parasitic Diptera larvae to be effectively controlled even in those parts of the body in which direct application is extremely difficult or virtually impossible.

A particularly advantageous method for control of the parasites comprises applying a suitable formulation containing the active substance to the animals to be treated by pouring onto the surface of the body (pour on or spot on). The advantages of this method are that it can be carried out very easily by those in charge of the animals, that it does not require any high expenditure on equipment and that it does not disturb the animals.

A further advantageous method comprises administering the active substance, to the animals to be treated, by means of an implant and thus achieving gradual liberation of the active substance.

The compounds of the formula I and their acid addition salts which are non-toxic to mammals are advantageously used in a concentration in the range of 10 to 50 mg/kg of body weight.

The compounds of the formula I and their acid addition salts which are non-toxic to mammals have, in particular, a good action against myiasis-producing larvae of insects of the order Diptera, which belong to the families Calliphoridae, Oestridae, Cuterebridae, Gasterophilidae, Sarcophagidae and Hypodermatidae, for example against larvae of *Lucilia* spec., *Cochlyomyia hominivorax, Chrysomyia bezziana, Hypoderma lineata, Hypoderma bovis, Dermatobia hominis, Oedemagena tarandi,* Gasterophilus spec., *Ostrus ovis, Rhinoestrus purpureus, Wohlfahrtia vigil* and Cuterebra spec.

The compounds of the formula I can be prepared according to processes known per se, by, for example, (a) reacting a 2-cyclopropylamino-4-amino-6-halogeno-s-triazine of the formula II, in which $R_1$ and $R_2$ are as defined for formula I and X is halogen, preferably chlorine, with ammonia or a primary and/or secondary amine of the formula V, in which $R_3$ and $R_4$ are as defined for formula I:

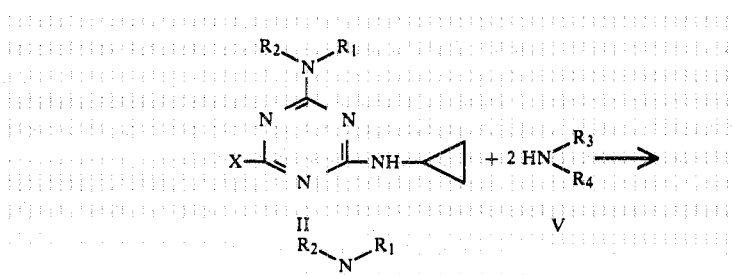

or (b) reacting a 2,4-diamino-6-halogeno-s-triazine of the formula III, in which $R_1$, $R_2$, $R_3$ and $R_4$ are as defined for formula I and X is halogen, preferably chlorine, with cyclopropylamine (formula VI):

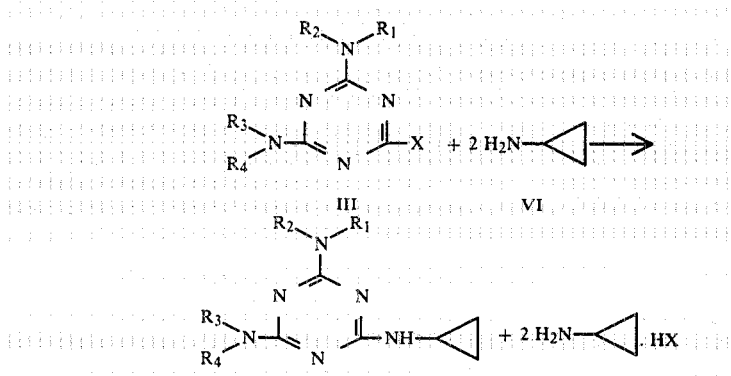

or (c) if, in the compounds of the formula I, $R_1$ has the same meaning as $R_3$ and $R_2$ has the same meaning as $R_4$, reacting a 2-cyclopropylamino-4,6-dihalogeno-s-triazine of the formula IV, in which X is halogen, preferably chlorine, with ammonia or a primary and/or secondary amine of the formula VII, in which $R'_1$ has the meaning defined for $R_1 = R_3$, as indicated for formula I, and $R'_2$ has the meaning defined for $R_2 = R_4$, as indicated for formula I:

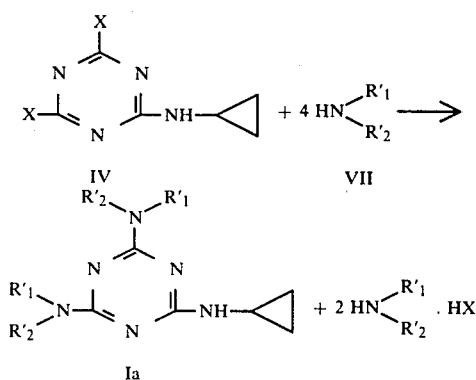

The replacement of the halogen atoms by ammonia or primary and/or secondary amines of the formulae V, VI and VII takes place by dissolving the starting materials of the formulae II, III and IV in inert solvents, for example acetone, acetone/water mixtures, methyl ethyl ketone, dioxan or dioxan/water mixtures, and reacting these mixtures under normal or, if desired, elevated pressure and at temperatures of 20°–150° C. and preferably 50°–140° C. with ammonia or primary and/or secondary amines.

The starting materials of the formulae II, III and IV are known in most cases or can be prepared analogously to known processes.

EXAMPLE 1

(a) 2Cyclopropylamino-4,6-diamino-s-triazine

A mixture of 100 g of 2-cyclopropylamino-4-amino-6-chloro-s-triazine, 51 g of ammonia and 500 ml of dioxan is heated at 140° C. in an autoclave for 24 hours. After cooling, the dioxan is removed by filtering with suction in vacuo and the crystalline residue is washed with water and dried. The crude product is recrystallised from methanol; melting point 219°–222° C.

(b) 2-Cyclopropylamino-4,6-diamino-s-triazine, salt with 2 mols of hydrochloric acid 25 g of 2-cyclopropylamino-4,6-diamino-s-triazine are dissolved in 2,000 ml of hot absolute ethanol. This solution is cooled to 15° C. and cooled further with ice and hydrogen chloride gas is then passed in until the solution is saturated. White crystals precipitate out. These are filtered off and the crude salt thus obtained is washed with a large amount of ether; melting point 195° C. (decomposition).

EXAMPLE 2

(a) 2-Cyclopropylamino-4-methylamino-6-amino-s-triazine

A mixture of 12.7 g of 2-cyclopropylamino-4-methylamino-6-chloro-s-triazine, 17.4 g of 28% aqueous ammonia solution and 30 ml of dioxan is heated at 140° C. in an autoclave for 4 hours. After cooling, the reaction mixture is poured into 350 ml of a solution, which has been cooled to 0° C., of potassium carbonate in water and extracted with 1:1 benzene/ether. After drying over sodium sulfate, the solvents are removed in vacuo and the residue is recrystallised from isopropanol/hexane; melting point 159°–162° C.

(b) 2-Cyclopropylamino-4-methylamino-6-amino-s-triazine, salt with 2 mols of hydrochloric acid 38 g of 2-cyclopropylamino-4-methylamino-6-amino-s-triazine are dissolved in 280 ml of chloroform. This solution is cooled with ice to 0°–5° C. and hydrogen chloride gas is passed in until the solution is saturated. White crystals precipitate out. 280 ml of ether are added to bring the precipitation to completion. The crude hydrochloride is filtered off and recrystallised from methanol; melting point 197°–199° C.

EXAMPLE 3

2,4,6-Tris-cyclopropylamino-s-triazine

A mixture of 20 g of 2-chloro-4,6-bis-cyclopropylamino-s-triazine, 10.1 g of cyclopropylamine and 80 ml of dioxan is heated at 140° C. in an autoclave for 22 hours. The reaction mixture is concentrated in vacuo to half its volume and 300 ml of water are added. The mixture is extracted with ethyl acetate, the product phase is dried over sodium sulfate and the solvents are removed in vacuo. The residue is recrystallised from dioxan/petroleum ether; melting point 75°–77° C.

The following compounds of the formula I can, for example, also be prepared in a manner analogous to that in Examples 1 to 3:

| No. | Compound | Melting point in °C. |
|---|---|---|
| 1 | 2-cyclopropylamino-4-amino-6-dimethyl-amino-s-triazine | 182–184 |
| 2 | 2,4-bis-(cyclopropylamino)-6-amino-s-triazine | 137–140 |
| 3 | 2-cyclopropylamino-4-methylamino-6-dimethylamino-s-triazine dihydrochloride | 164–165 |
| 4 | 2-cyclopropylamino-4,6-bis-(dimethyl-amino)-s-triazine | 140–142 |
| 5 | 2-cyclopropylamino-4-amino-6-ethylamino-s-triazine | 141–145 |
| 6 | 2-cyclopropylamino-4-amino-6-ethylamino-s-triazine dihydrochloride | 199–200 |
| 7 | 2,4-bis-(cyclopropylamino)-6-dimethyl-amino-s-triazine | 136–137 |

The compounds of the formula I or their acid addition salts which are non-toxic to mammals can be used as pure active substance or together with suitable carriers and/or adjuvants. Suitable carriers and adjuvants can be solid or liquid and are the substances conventionally employed in the art of formulation, for example natural or regenerated substances, solvents and/or dispersants.

Compositions which contain the active substance or an acid addition salt thereof which is non-toxic to mammals can be prepared in a manner known per se by dissolving the active substance in suitable solvents and/or intimately mixing and/or grinding the active substances with suitable carriers, if desired with the addition of dispersants or solvents which are inert towards the active substances. The active substances can be processed to the following formulations:

Solid formulations: dusts;
Liquid formulations:
(a) Active substance concentrates which are dispersible in water: wettable powders, pastes and emulsions;
(b) Solutions: injectable and pour-on.

Solid formulations are prepared by mixing the active substances with solid carriers. Suitable carriers are, for example, kaolin, talc, bolus, loess, chalk, limestone, ground limestone, attaclay, diatomaceous earth, precipitated silica, alkaline earth silicates, sodium and potassium aluminium silicates (feldspars and mica), calcium and magnesium sulfates, magnesium oxide, ground synthetic materials, ground vegetable products, such as corn meal, sawdust, cellulose powder, residues of plant extractions, activated charcoal, polymers conventionally used galenically and the like. These substances can either be used singly or in admixture with one another.

Water-dispersible active substance concentrates, i.e. wettable powders, pastes and emulsifiable concentrates, are compositions which can be diluted with water to the desired concentration. They consist of active substance, carrier, optionally additives which stabilise the active substance, surface-active substances and antifoams and, if appropriate, solvents. Wettable powders and pastes are obtained by mixing and grinding the active substances with dispersants and pulverulent carriers in suitable devices until homogeneity is attained. Suitable carriers are, for example, those already mentioned for the solid formulations. In some cases it is advantageous to use mixtures of different carriers. Dispersants which can be used are, for example: condensation products of sulfonated naphthalene and sulfonated naphthalene derivatives with formaldehyde, condensation products of naphthalene or naphthalenesulfonic acids with phenol and formaldehyde, as well as alkali metal, ammonium and alkaline earth metal salts of ligninsulfonic acid, and also alkylarylsulfonates, alkali metal and alkaline earth metal salts of dibutylnaphthalenesulfonic acid, fatty alcohol sulfates, such as salts of sulfated hexadecanols, heptadecanols, octadecanols and salts of sulfated fatty alcohol glycol ethers, the sodium salt of oleyl methyl tauride, ditertiary ethylene glycols, dialkyldilaurylammonium chloride and fatty acid alkali metal and alkaline earth metal salts.

Suitable anti-foams are, for example, silicone oils. The active substances are so mixed, ground, sieved and strained with the additives mentioned above that the solid particle size does not exceed 0.02 to 0.04 in wettable powders and 0.03 mm in pastes. Emulsifiable concentrates and pastes are produced using dispersants, such as those cited previously above, organic solvents and water. Examples of suitable solvents are alcohols, dimethylsulfoxide and mineral oil fractions which boil between 120° and 350° C. The solvents must be practically odourless and inert towards the active substances.

Furthermore, the compositions of the invention can be used in the form of solutions. For this purpose suitable organic solvents or solvent mixtures or water are admixed to the active substance or several active substances of the general formula I. Aliphatic and aromatic hydrocarbons, carboxylic acid esters, ethers and mineral oils, singly or in admixture, can be used as organic solvents.

The domestic animals and productive livestock which can be parasite carriers can be treated in various ways, for example using an atomised spray (direct spraying by hand; spray run or a close-set or wide-set row of spray jets), a dip, dusting installations, pour on (total or partial), injectable solutions, an implant or a collar.

When using an atomised spray, formulations which can be employed are, for example, wettable powders or emulsifiable concentrates. Emulsifiable concentrates and wettable powders can likewise be chosen for use with a close-set row of spray jets or a dip. Formulations which can be used for the pour on method are, for example, wettable powders, emulsifiable concentrates or solutions of the active substance in paraffin oil, corn oil or rape oil. Injectable solutions are obtainable by dissolving the active substance in, for example, diethyl succinate. Implants can consist, for example, of gelatin capsules filled with active substances or of a solid formulation which contains the active substance together with synthetic materials conventionally used galenically. Collars which can be used are, for example, those made of synthetic materials into which the active substance is incorporated in a suitable form.

Implants or collars are particularly suitable forms of application for treatment in those cases in which slow release of the active substance is desired.

The active substances of the formula I or their acid addition salts which are non-toxic to mammals can be formulated, for example, as follows:

Dust:
The following substances are used to formulate a 5% dust:

5 parts of active substance
1 part of highly disperse silica
94 parts of talc.

The active substances are mixed with the carriers and the mixture is ground.

Wettable powder:

50 parts of active substance are mixed with 5 parts of a dispersant, for example sodium ligninsulfonate, 5 parts of a wetting agent, for example dibutylnaphthalenesulfonic acid, 10 parts of silica and 30 parts of kaolin and the mixture is finely ground.

Emulsifiable concentrate:

20 parts of active substance are mixed with 20 parts of emulsifier, for example a mixture of alkylaryl polyglycol ether with alkylarylsulfonates, and 60 parts of solvent, until the solution is completely homogeneous. With water, this concentrate gives an emulsion of any desired concentration.

Solutions

Solution for the pour on method 10 parts of active substance
55 parts of "Solketal®" (2,2-dimethyl-4-hydroxymethyl-1,3-dioxolane)
20 parts of benzyl benzoate
15 parts of polyethylene glycol 300

The active substance is dissolved in the mixture of Solketal and polyethylene glycol 300 with continuous stirring and warming and the benzyl benzoate is then added.

Injection solution 10.0 parts of active substance
3.6 parts of acetic acid
86.4 parts of water for injection The acetic acid and the water are added to the active substance and the mixture is stirred until everything has dissolved. The solution is then filtered and sterilised by a suitable method. pH of the solution: 5.0.

Other biocidal active substances or compositions which are inert towards the active substances and acceptable for the animals to be treated can be admixed to the compositions described.

TEST 1

Pour on application to cattle

5–100 ml of a suitable formulation, which contains up to 100 mg/kg of live weight of an active substance of the formula I or of a non-toxic acid addition salt thereof, are poured onto the backs of the cattle. Blood samples are now taken from the jugular vein at specific intervals. These samples are mixed with a specific culture medium and freshly hatched larvae I of *Lucilia sericata* are applied to this mixture. The larvicidal action is assessed after 72 hours.

In this test, the compounds of the formula I and their non-toxic acid addition salts show a pronounced larvicidal action.

TEST 2

Use of injectable solutions on cattle

Cattle are injected subcutaneously with a suitable formulation of an active substance of the formula I or of a non-toxic acid addition salt thereof. Blood samples are now taken from the jugular vein at specific intervals. These samples are mixed with a specific culture medium and freshly hatched larvae I of *Lucilia sericata* are applied to the mixture. The larvicidal action is assessed after 72 hours.

In this test, the compounds of the formula I and their non-toxic acid addition salts show a pronounced larvicidal action.

What is claimed is:

1. A procedure for treating domestic animals and productive livestock belonging to the class of Mammalia for systemic control of tissue-parasitic insect larvae of the order of Diptera, which comprises parenteral or transcutaneous administration, to the animals to be treated, of an effective dose of an active substance of the general formula I

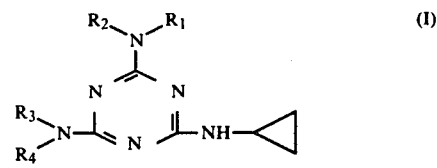

in which $R_1$ is hydrogen, methyl, ethyl or cyclopropyl, $R_2$ is hydrogen or methyl, $R_3$ is hydrogen, methyl or cyclopropyl and $R_4$ is hydrogen or methyl, or of an acid addition salt thereof which is non-toxic to mammals or of a composition which contains the active substance or an acid addition salt thereof which is non-toxic to mammals.

2. A procedure according to claim 1, wherein the active substance used is 2,4-diamino-6-cyclopropylamino-s-triazine.

3. A procedure according to claim 1, wherein the application is carried out dermally by pouring onto the surface of the body of the animals to be treated.

4. A procedure according to claim 1, wherein the application is made by implanting a material which is readily acceptable to the animal to be treated and which is provided with an active substance, an acid addition salt thereof which is non-toxic to mammals or a composition containing the active substance or an acid addition salt thereof which is non-toxic to mammals.

* * * * *